(12) United States Patent
Stevenson et al.

(10) Patent No.: US 7,623,336 B2
(45) Date of Patent: Nov. 24, 2009

(54) FEEDTHROUGH CAPACITOR HAVING REDUCED SELF RESONANCE INSERTION LOSS DIP

(75) Inventors: Robert A. Stevenson, Canyon Country, CA (US); Warren S. Dabney, Odenton, MD (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 426 days.

(21) Appl. No.: 11/756,038

(22) Filed: May 31, 2007

(65) Prior Publication Data

US 2007/0279834 A1 Dec. 6, 2007

Related U.S. Application Data

(63) Continuation-in-part of application No. 11/558,349, filed on Nov. 9, 2006, and a continuation-in-part of application No. 11/423,073, filed on Jun. 8, 2006.

(60) Provisional application No. 60/803,672, filed on Jun. 1, 2006.

(51) Int. Cl.
*H01G 4/35* (2006.01)

(52) U.S. Cl. ............... 361/302; 361/303; 361/305; 361/306.1; 361/306.3; 361/321.2; 607/5; 607/7; 607/9

(58) Field of Classification Search ............... 361/302, 361/303–305, 306.1, 306.3, 321.1, 321.2; 607/5, 7, 9
See application file for complete search history.

(56) References Cited

U.S. PATENT DOCUMENTS

| 4,424,551 | A | 1/1984 | Stevenson et al. |
| 5,905,627 | A | 5/1999 | Brendel et al. |
| 5,999,398 | A * | 12/1999 | Makl et al. ............... 361/302 |
| 6,008,980 | A | 12/1999 | Stevenson et al. |
| 6,275,369 | B1 * | 8/2001 | Stevenson et al. ........... 361/302 |
| 6,349,025 | B1 * | 2/2002 | Fraley et al. ............... 361/302 |
| 6,414,835 | B1 * | 7/2002 | Wolf et al. ............... 361/302 |
| 6,643,903 | B2 | 11/2003 | Stevenson et al. |
| 6,765,779 | B2 | 7/2004 | Stevenson et al. |

OTHER PUBLICATIONS

Robert A. Stevenson, P.E., Mike Lowder, Improved EMI Filter Insertion Loss Test Methods, Equipment and Fixtures, CARTS 96: 16th Capacitor and Resistor Technology Symposium, Mar. 11-15, 1996.
Bob Stevenson, PE, Dissipation Factor Testing is Inadequate for Medical Implant EMI Filters and Other High Frequency MLC Capacitor Applications, CARTS 2003: 23rd Capacitor and Resistor Technology Symposium, Mar. 31-Apr. 3, 2003.
Bob Stevenson, EMI Filters for Medical Devices, slide presentation given at 2000 Medical Device and Manufacturing Symposium, Anaheim, CA.

* cited by examiner

*Primary Examiner*—Nguyen T Ha
(74) *Attorney, Agent, or Firm*—Kelly Lowry & Kelley LLP

(57) ABSTRACT

The self-resonance insertion loss dip of a feedthrough capacitor is reduced or eliminated by raising the equivalent series resistance of the capacitor, thus minimizing the capacitor Q. The equivalent series resistance of the capacitor can be raised by forming voids in the active and/or ground electrode plates of the capacitor. The electrode plates may be formed so as to have a relatively reduced thickness, or a relatively increased thickness. A conductive material having a relatively high resistivity may be used to form the active and/or ground electrode plates of the capacitor. Alternatively, the conductive material forming the electrode plates may have a dielectric material added thereto.

26 Claims, 9 Drawing Sheets

FIG. 6
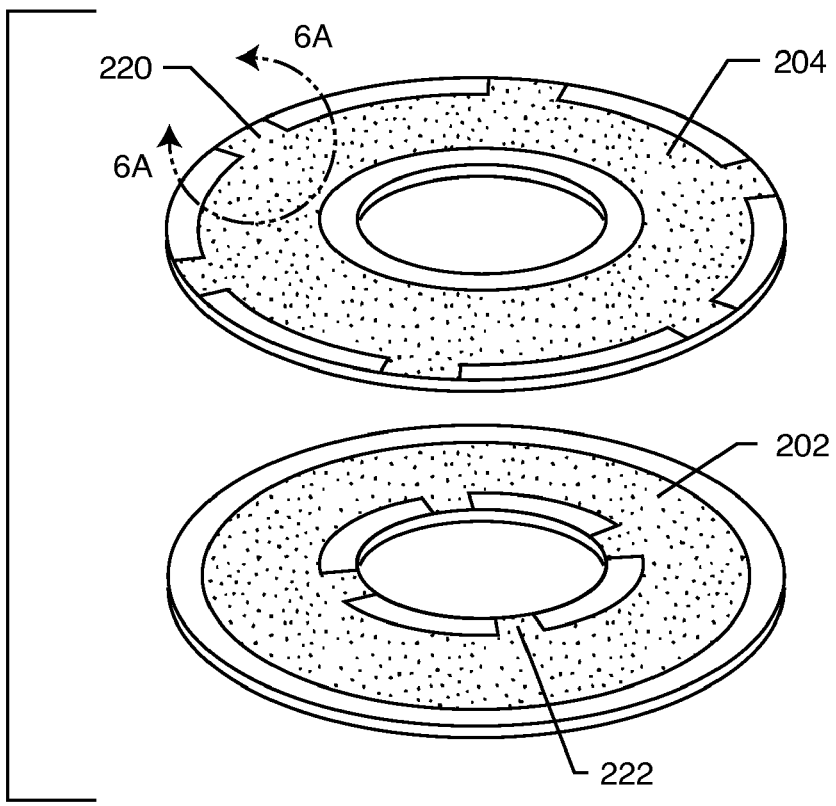
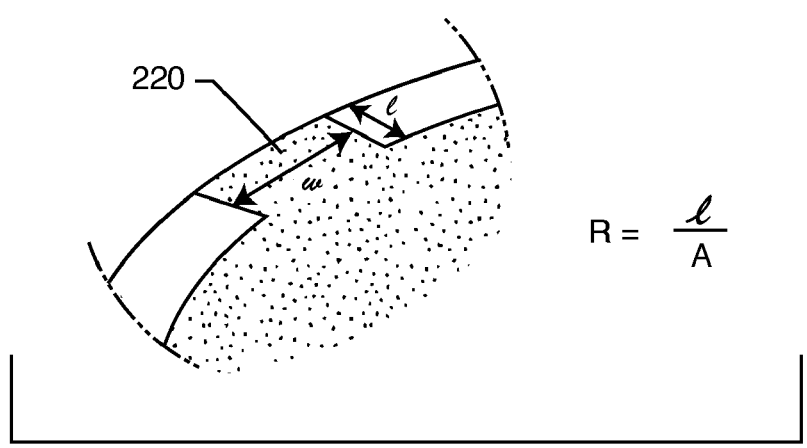
$R = \dfrac{\ell}{A}$
FIG. 6A

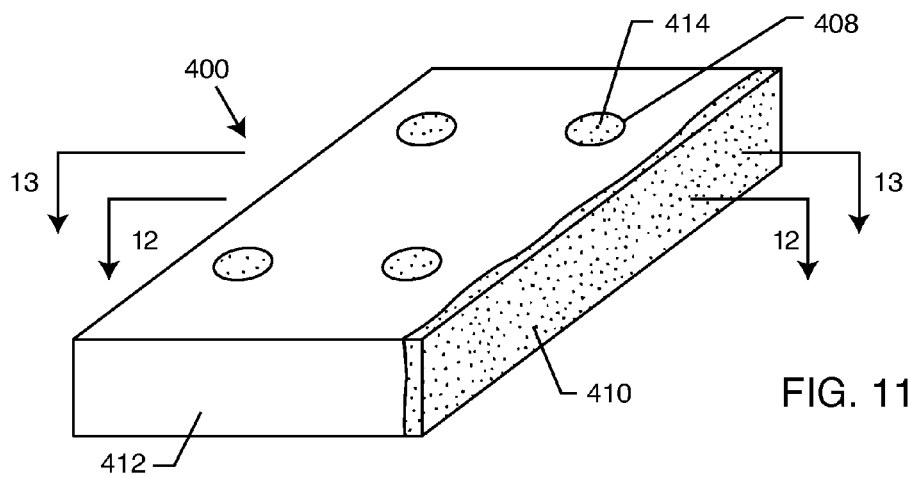
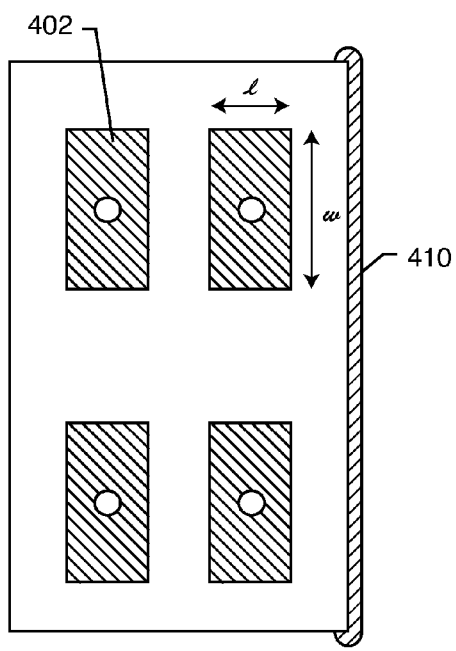
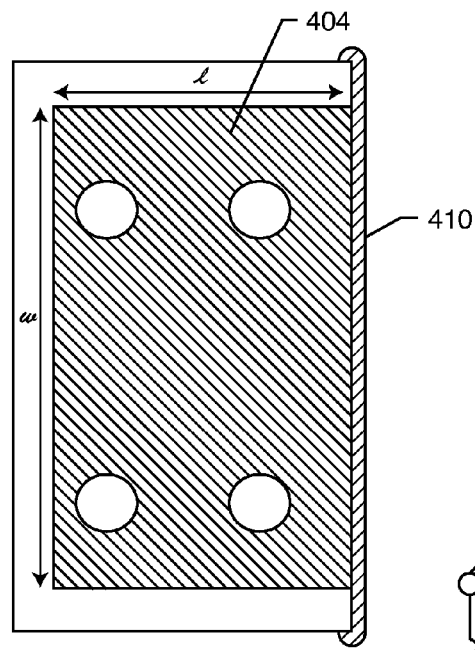
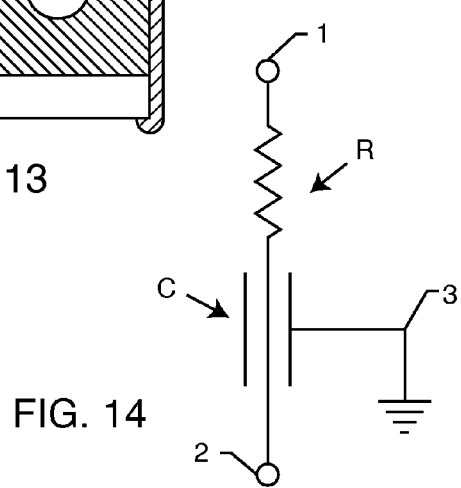
FIG. 11
FIG. 12
FIG. 13
FIG. 14

FEEDTHROUGH CAPACITOR HAVING REDUCED SELF RESONANCE INSERTION LOSS DIP

BACKGROUND OF THE INVENTION

The present invention generally relates to feedthrough capacitors. More particularly, the present invention relates to feedthrough capacitors which have been constructed in such a manner so as to substantially reduce, or even completely eliminate, the self-resonance insertion loss dip.

Feedthrough capacitors are well known in the prior art. Feedthrough capacitors are different from chip monolithic ceramic capacitors (MLCC). Rectangular chip capacitors are two-terminal devices and therefore have significant internal inductance. Feedthrough capacitors are three-terminal devices that act as transmission lines and therefore have very low internal inductance. Feedthrough capacitors are very useful for electromagnetic interference (EMI) filters in that they provide substantial attenuation over a very broad frequency range. Feedthrough capacitors can be ceramic single or multilayer, tubular ceramic, wound film types, wound impregnated paper types, thick film deposited, thin film deposited, glass ceramics and even stabilized multi-component systems. As used herein, the term "feedthrough capacitor" shall be inclusive of all of these and equivalent technologies. For simplicity, the drawings that illustrate the inventive concepts herein are shown for multilayer ceramic feedthrough capacitors. It will be obvious to those skilled in the art that these novel design principles may be adapted to all other feedthrough capacitor technologies.

A limitation to all prior art feedthrough capacitors is their tendency to exhibit one or more self-resonant dips. These self-resonant dip characteristics are not completely understood, but at least in part has to do with the interaction of the internal electrode plates and their own self-inductance in a transmission line configuration. Self-resonant dips are a very undesirable characteristic of feedthrough capacitors because they reduce the amount of effective attenuation at the resonant dip frequencies. Accordingly, less protection to circuits is provided from electromagnetic interference.

The inventors have noted that the higher the Quality Factor, or Q, of the capacitor (that is, the lower its internal losses), the sharper the resonant dips tend to be. A paper entitled *Improved EMI Insertion Loss Test Methods, Equipment and Fixtures*, given at the 1996 CARTS Symposium, (incorporated by reference), describes a method of fixturing various types of EMI filters and feedthrough capacitors, and includes a substantial discussion of resonant dips. An example is given of a United States defense standard, MIL-PRF-28861 (MIL-SPEC), filter that had a specification limit of 20 dB, but because of the self-resonant dip of the feedthrough capacitor, only 13 dB was achieved at this particular frequency. No manufacturer found a way to eliminate the self-resonant dip, thus the MIL-SPEC was modified to allow for the self-resonant dip. Of course, this was not ideal.

Accordingly, there is a need for a feedthrough capacitor in which the amplitude of the self-resonance insertion loss dip is significantly reduced or even eliminated. The present invention fulfills this need and provides other related advantages.

SUMMARY OF THE INVENTION

The present invention relates to feedthrough capacitors having reduced high frequency Q, and thus have a substantially reduced, if not eliminated, self-resonant dip. Moreover, the present invention relates to methodologies for modifying the feedthrough capacitor in order to reduce its Q by increasing its Equivalent Series Resistance (ESR) so as to reduce the capacitor's self-resonant dip.

In accordance with the present invention, the novel feedthrough capacitor generally comprises a dielectric body having a passageway therethrough, active electrode plates disposed within the body and having an end terminating at the passageway, and ground electrode plates disposed within the body in spaced relation to the active electrode plates. The ground electrode plates have a portion terminating at a point spaced from and in electrical isolation from the active electrode plates termination. The capacitor Quality Factor (Q) is relatively minimized by raising the equivalent series resistance of the capacitor, whereby the self-resonance insertion loss dip of the capacitor is reduced or eliminated.

In particular, the capacitor Quality Factor (Q) is reduced by forming voids within the active and/or ground electrode plate(s). Typically, the active and ground electrode plates each include an outer boundary and an inner boundary adjacent to the capacitor passageway. The voids are disposed between the outer and inner boundaries. The voids may comprise apertures, gaps, slits or spokes formed in the active and/or ground electrode plate, or a pattern of such voids.

Controlling the resistivity of the capacitor and/or ground electrode plate(s) may be done by controlling their cross-sectional area (width by thickness). In order to increase the equivalent series resistance of the capacitor, the thickness of the active and/or ground electrode plate(s) may be modified. In this regard, the active and/or ground electrode plate(s) may be of a relatively reduced thickness. For example, the active and/or ground electrode plate(s) may be formed between 0.1 nanometer and 10 microns in thickness. Alternatively, the active and/or ground electrode plates may be of a relatively increased thickness but made of materials with a relatively high resistivity.

In addition, or alternatively, the active and/or ground electrode plates may be comprised of a conductive material having a relatively high resistivity. For example, the active and/or ground electrode plates may be comprised of platinum, a platinum alloy, palladium, palladium-silver alloys, or ternary systems consisting of gold, platinum and palladium. Base metal electrodes (such as nickel) may be also used.

Moreover, the resistivity of the capacitor active and/or ground electrode plates may be controlled by controlling their cross-sectional areas. Aside from controlling the thickness of the active and/or ground electrode plate, the active and/or ground electrode plate may have a relatively greater length than width.

The equivalent series resistance of the capacitor can also be increased, thus decreasing the Q of the capacitor, by providing active and/or ground electrode plates comprised of a conductive material having a dielectric material added thereto. For example, the conductive material may comprise electrode ink having dielectric powder or equivalent fillers added thereto. This is known as reducing the metal loading of the electrode ink system.

Yet other ways of increasing the equivalent series resistance of the capacitor so as to reduce its Q, include providing a resistor in series with the capacitor, or selecting a material for the dielectric body of the capacitor which has a high dielectric loss tangent at a selected frequency.

Adding series resistances can be accomplished my adding novel tab structures to the electrodes where the connection to the outside (ground) or inside diameter (active) electrode terminations are made and/or by increasing the resistivity of the feedthrough capacitor ground and/or active electrode plate metallization material itself.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 6 is a perspective view of active and ground electrode plates similar to those previously shown in FIGS. 4 and 5, except that the electrode plates have been modified to add tab areas;

FIG. 6A is an enlarged fragmented view of the area indicated by line 6A-6A in FIG. 6;

FIG. 11 is a perspective view of a rectangular quadpolar feedthrough capacitor embodying the present invention, having a ground termination on one side;

FIG. 12 is a cross-sectional view taken generally along line 12-12, illustrating the configuration of the active electrode plates;

FIG. 13 is a cross-sectional view taken generally along line 13-13 of FIG. 11, illustrating the configuration of the ground electrode plates;

FIG. 14 is an electrical schematic diagram of a unipolar feedthrough capacitor having a resistive element in series with a capacitor, in accordance with the present invention.

DETAILED DESCRIPTION OF THE PREFERRED EMBODIMENTS

As shown in the accompanying drawings for purposes of illustration, the present invention resides in feedthrough capacitors designed and manufactured in such a manner that the quality factor, or Q, of the capacitor is relatively minimized by increasing the equivalent series resistance of the capacitor, so as to reduce or even eliminate the self-resonance insertion loss dip of the capacitor.

Figure 1:
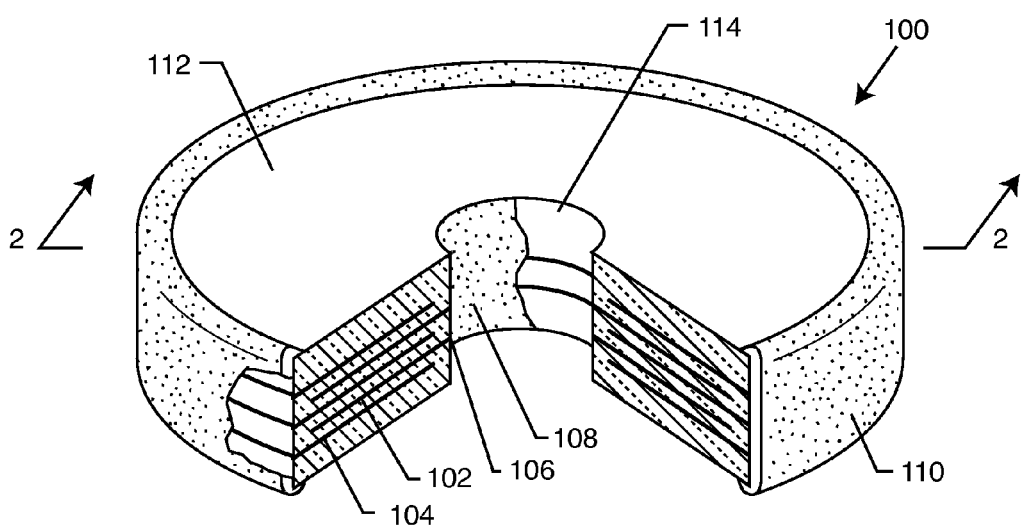
FIG. 1 is a partially sectioned perspective view of a prior art unipolar feedthrough capacitor.
Figure 2:
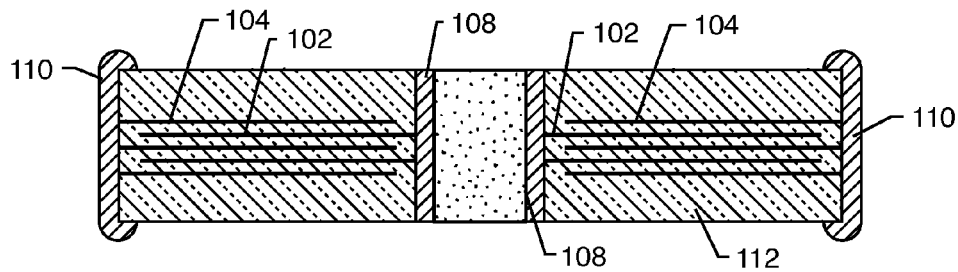
FIG. 2 is a cross-sectional view taken generally along line 2-2 of FIG. 1.
Figure 2A:
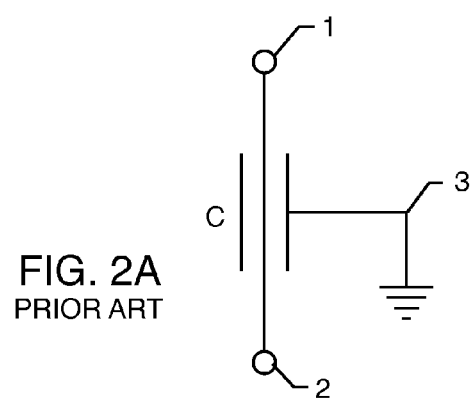
FIG. 2A is an electrical schematic diagram of the capacitor of FIGS. 1 and 2.

With reference to FIGS. 1, 2 and 2A, a prior art unipolar feedthrough capacitor 100 is illustrated. This is a multilayered coaxial capacitor, which is well known in the art. One of its advantages is that it can operate at a very high frequency. This is due to its coaxial transmission line nature and the fact that it has very low internal inductance.

The capacitor 100 includes overlapping circular electrode plate sets 102 and 104. Electrode plate set 102 is known as the active electrode plate set and has an edge 106 which terminates in contact with metallization 108 lining the capacitor inside passageway for a feedthrough terminal pin or the like. The ground electrode plate set 104 is electrically coupled to an outside diameter metallization 110. The active electrode plates 102 and the ground electrode plates 104 are separated by dielectric material comprising the dielectric body 112. The capacitor 100 illustrated in FIGS. 1 and 2 is unipolar in that it has a single passageway 114 extending through the dielectric body 112 thereof.

Such feedthrough capacitors 100 are generally made out of the same materials as monolithic chip capacitors (MLCCs). However, what differentiates feedthrough capacitors from MLCCs are the passageways 114 therethrough. The feedthrough capacitor 100 acts as a three terminal transmission line device, as shown in the electrical schematic diagram in FIG. 2A. An incident radio frequency (RF) signal at point 1 is greatly attenuated by the time it reaches point 2. The ground electrode plates 104 are schematically shown grounded at point 3. The metallized surface 108 connects the active electrode plates 102 together, and the outer metallization 110 conductively couples and connects the ground electrode plates 104 together, and allows convenient points of electric connections, such as by soldering or conductive thermal setting adhesives or the like. Such prior art feedthrough capacitors are often used in conjunction with electromagnetic interference (EMI) filters for active implantable medical devices (such as shown and described in U.S. Pat. Nos. 4,424,551; 5,905,627; 6,008,980; 6,643,903; 6,765,779, the contents of which are incorporated herein by reference, although there are other applications where such feedthrough capacitors are used.

As mentioned above, prior art feedthrough capacitors have a limitation as they tend to exhibit a self-resonant dip. Although not completely understood, it is believed to arise due, at least in part, to the interaction of the electrode plates 102 and 104 and their own self-inductance in a transmission line configuration, as illustrated in FIG. 2A. In the self-resonant dip, the attenuation of the device degrades thereby providing less attenuation to EMI signals in the resonant dip portion. This is a serious problem for designers which often necessitates the addition of a second element, such as an inductor, to make up for the performance loss of the self-resonant dip of the capacitor.

It has been found that increasing the equivalent series resistance (ESR) of the capacitors, such as by changing the electrode resistance to decrease the Q of the capacitor in a controlled manner and by a precise amount, can reduce or even eliminate the capacitor self-resonant dips, yet still achieve the desired high frequency performance. However, as discussed in a paper entitled *Dissipation Faction Testing Is Inadequate For Medical Implant EMI Filters And Other High Frequency MLC Capacitor Applications*, given at the 2003 CARTS Symposium, (incorporated herein by reference), one cannot increase the ESR of the capacitor too much or serious degradation and serious loss performance will occur. Thus, the present invention includes a methodology for decreasing the feedthrough capacitor Q in a precise way, such that the self-resonant dips of the capacitor are reduced or eliminated, while at the same time preserving nearly ideal feedthrough capacitor performance throughout the broad frequency band.

Figure 3:
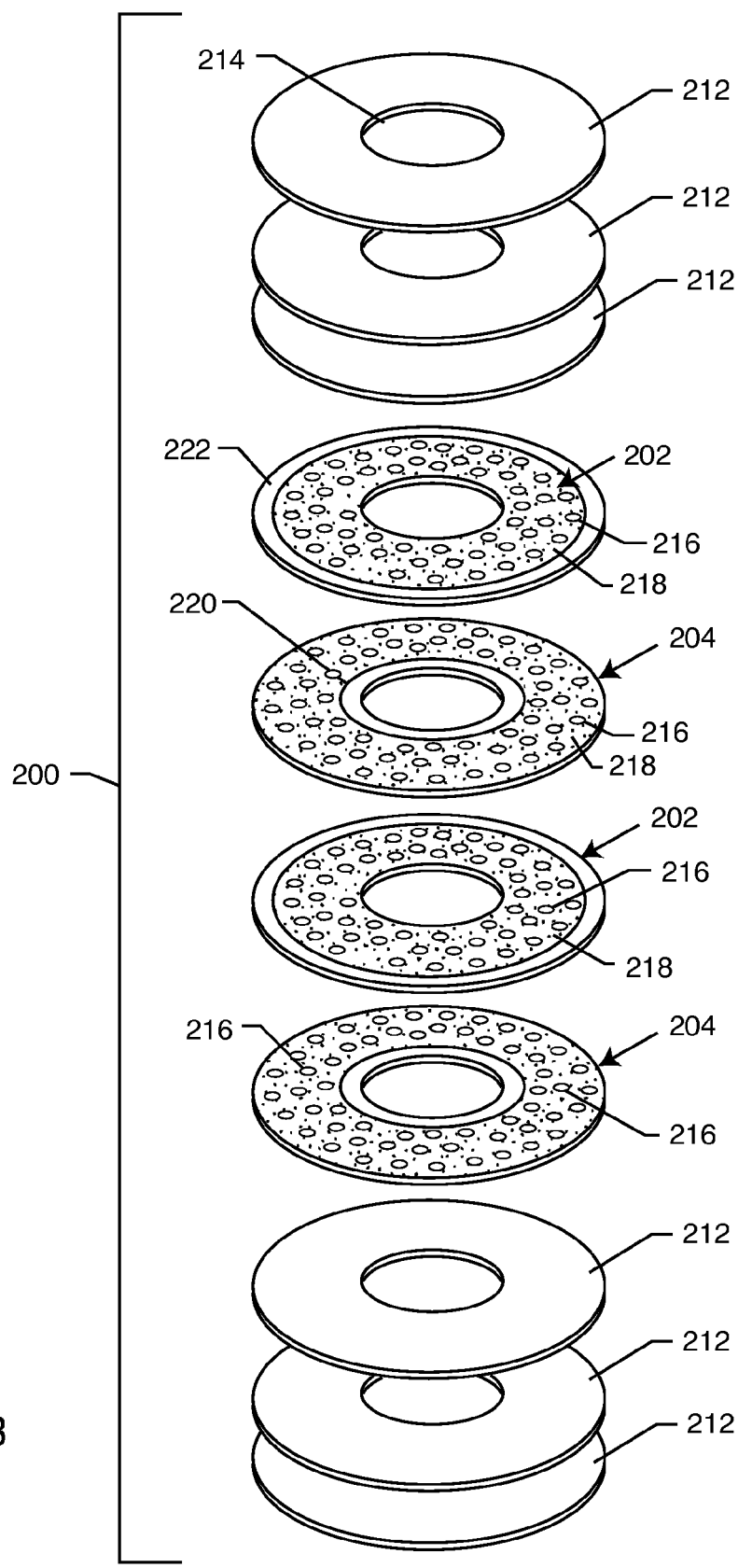
FIG. 3 is an exploded perspective view of a capacitor similar to that shown in FIGS. 1 and 2, illustrating an improved capacitor having voids in electrode plates to reduce the capacitor Q, in accordance with the present invention.

With reference to FIG. 3, feedthrough capacitors typically include one or more layers of dielectric material 212, sometimes referred to as thin cover sheets, comprised of ceramic or other dielectric material. Such capacitors are typically formed in a process wherein thin layers of the dielectric material 212 are sequentially deposited. During the construction of the capacitor, active electrode plates 202 and ground electrode plates 204 are formed on ceramic tape layers and placed in alternating layers. This is done using an electrode plate ink comprised of the desired electrode plate material, which is typically conductive. These alternating layers can be stacked to achieve the desired capacitance required. This is finished off by dielectric cover sheets 212, shown at the top portion of FIG. 3. These are typically pressed, laminated and then fired to a high temperature to form a rugged monolithic structure, such as the capacitor 100 illustrated in FIG. 1. A metallization band, such as metallization 108, is formed along the one or more inner passageways, and typically an outer metallization band, such as metallization 110, is then added for convenient electrical attachment, as described above.

In accordance with the present invention, voids 216 are formed in the conductive material 218 comprising the one or more active and/or ground electrodes 202 and 204, as illustrated in FIG. 3. Typically, the plurality of voids 216 are formed in the electrode plate 202 and/or 204 between an inner boundary 220 and an outer boundary 222 thereof. As shown, the voids 216 have been formed in both the active electrode plates 202 as well as the ground electrode plates 204. However, it is not necessary to form the voids 216 in both the active and ground plates 202 and 204, or even in all of the electrode plates of a given set 202 or 204. In a preferred embodiment, however, one would form the voids 216 in both sets of electrode plates 202 and 204. The presence of the voids 216 in the capacitor electrode plates 202 and/or 204 increase the equivalent series resistance (ESR) of the capacitor. Increasing the ESR effectively decreases and minimizes the Q of the capacitor, and when done in a selective and controlled and precise manner, substantially reduces, or even eliminates, the self-resonance insertion loss dip of the capacitor.

In one embodiment, the voids 216 are formed in the electrode plates 202 and 204 by means of adding blockages to a silk screen pattern that is used to squeegee the electrode ink paste material 218 onto the ceramic tape carrier, or other layer of dielectric material 212. The obstructions, which may be in the form of solid dots, prevent the deposition of the electrode ink on the ceramic carrier at that location. Once this goes through a series of firing cycles, the result is an electrode 202 or 204 that is full of "Swiss-cheese-type" voids 216, as illustrated in FIG. 3. As mentioned above, this has the effect of increasing the resistivity (equivalent series resistance) of the capacitor's internal electrodes 202 and 204, while at the same time having very little effect on its capacitance value. This is due to the fact that an electrostatic space charge still occurs across the voids 216 and between the electrode plates 202 and 204 of opposite polarity.

Figure 4:
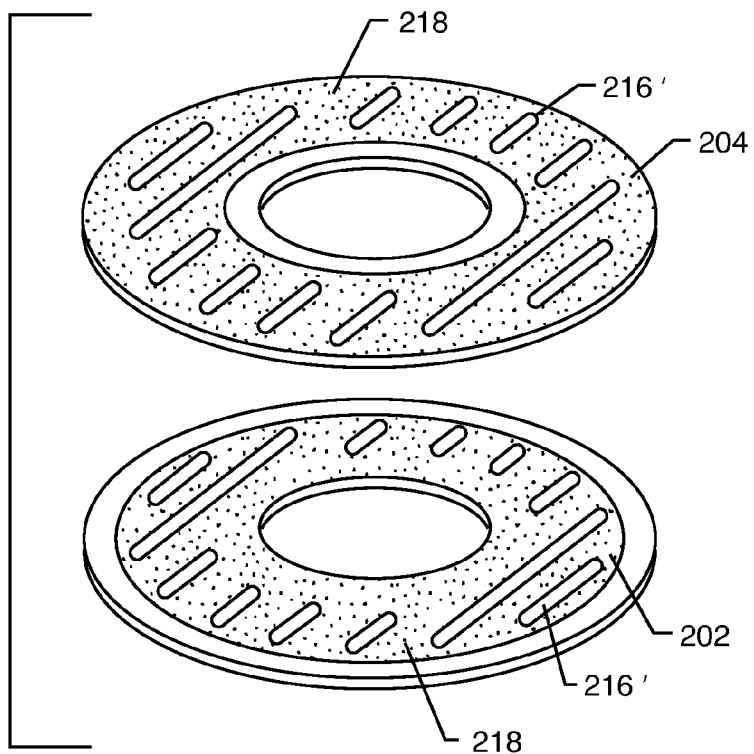
FIG. 4 is a perspective view of an active and a ground electrode plate having slits formed therein in accordance with the present invention.
Figure 5:
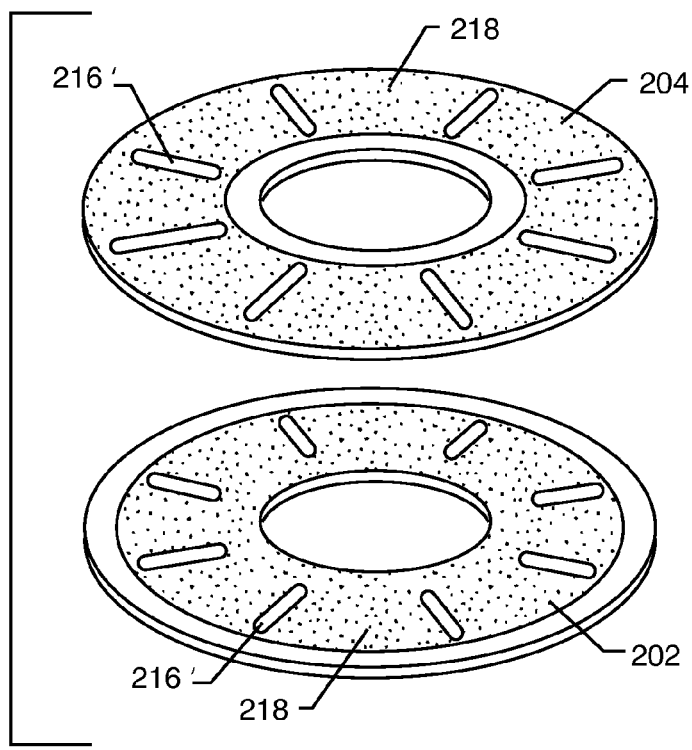
FIG. 5 is a perspective view of an active and a ground electrode plate having a spoke void arrangement, in accordance with the present invention.

With reference to FIGS. 4 and 5, it will be appreciated by those skilled in the art that the voids 216 can be of many different shapes, sizes, and patterns. For example, the active and ground electrode plates 202 and 204 illustrated in FIG. 4 are formed with conductive electrode material 218 having voids 216' in the form of spaced-apart slits. In FIG. 5, the slits 216' are arranged so as to form a spoke pattern. It will be appreciated by those skilled in the art that the voids could comprise apertures, gaps, slits or spokes, of varying sizes, configurations, patterns, etc. The important aspect is that there still exists an electrostatic space charge across the void 216, while increasing the resistivity, or ESR, of the electrode plate 202 or 204.

FIG. 6 is a drawing similar to those previously illustrated in FIGS. 4 and 5 except that the electrode plates have been especially modified to add tab areas 220 and 222. Although not shown, the electrode plates 202 and 204 could include the voids 216 described previously. In FIG. 6, one can see that for the ground electrode plate 204, tab areas 220 have been added which tend to add an extended tab(s) connection area between the electrode plate 204 and its outer metallization surface 110 (not shown). The tabs 220 can be varied in width and in length and in numbers so as to control their series resistance and series inductance to the ground electrode plate 204. This allows the designer great latitude in controlling the overall equivalent series resistance and equivalent series inductance at selected frequencies such as to cancel out the self-resonant dip as described herein. This can also be done for the active electrode plate 202. A number of tabs 222 can be added which have the same function as previously described for the ground electrode plate. In this way, by limiting the contact area to the inside diameter metallization 108 (not shown) one can control the resistance in series with said electrode plate and thereby increase its overall equivalent series resistance (ESR).

FIG. 6A is an exploded sectional view taken generally from 6A-6A from FIG. 6. This shows a blow-up of the tab area 220 showing that it has both width and length. The overall resistance of this tab is given by the resistivity of the material times its length divided by its cross-sectional area A. The length is shown as l and the width is shown as W. The cross-sectional area is W times its deposited thickness. One can control the series resistance with, in this case, the ground electrode plate 204 by adjusting the width of the tab, the deposited thickness of the tab and the length of the tab 220.

Figure 7:
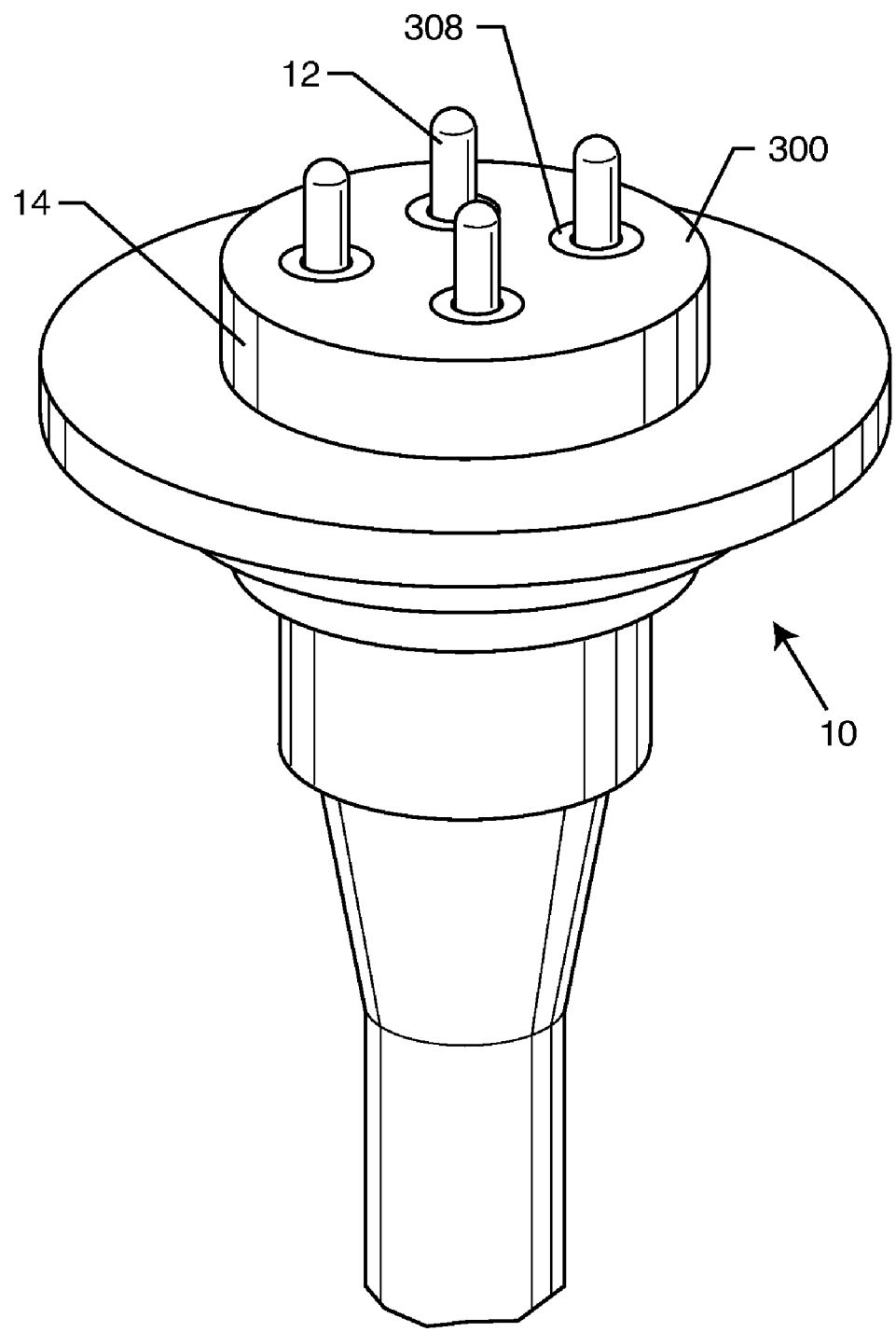
FIG. 7 is a perspective view of a quadpolar feedthrough capacitor embodying the present invention surface, forming a portion of an exemplary filtered feedthrough terminal.
Figure 8:
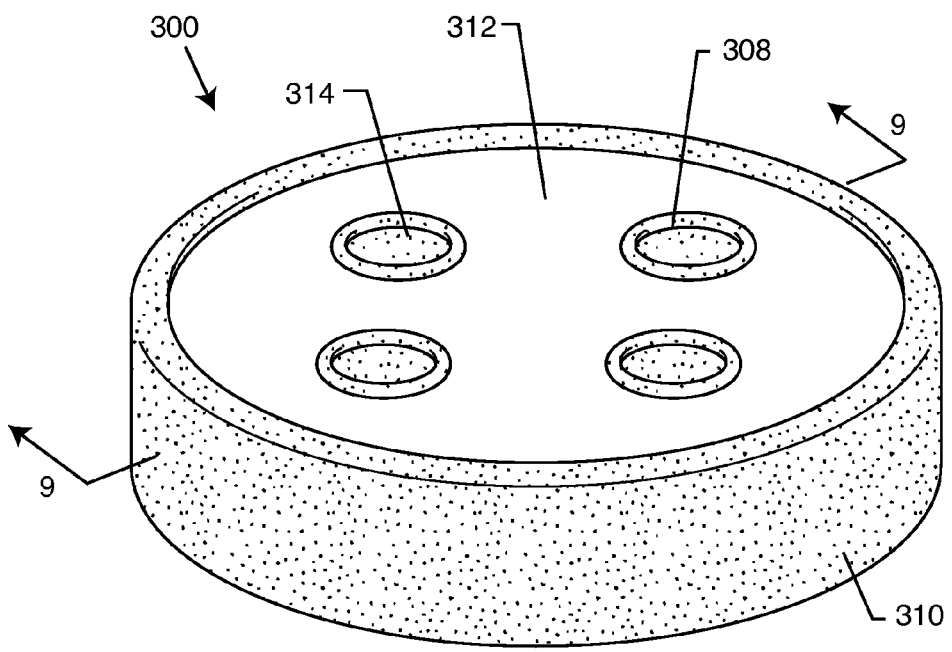
FIG. 8 is a perspective view of the quadpolar feedthrough capacitor of FIG. 7.
Figure 9:
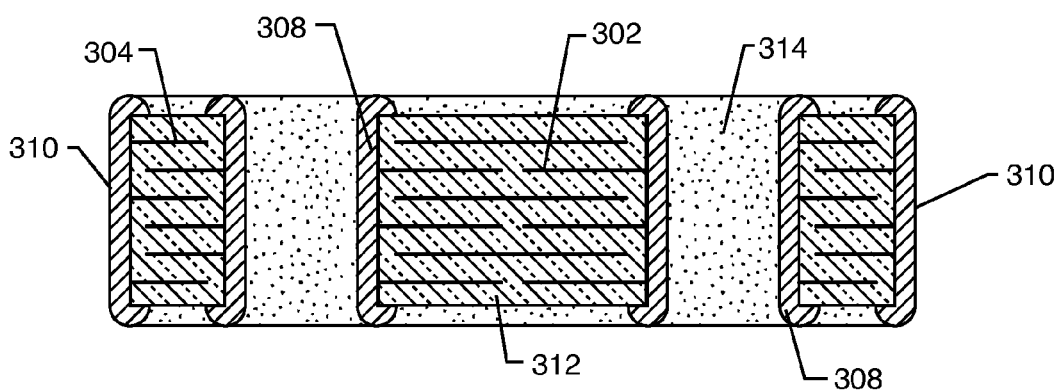
FIG. 9 is a cross-sectional view taken generally along line 9-9 of FIG. 8.

With reference now to FIGS. 7-9, a surface mounted quad-polar feedthrough capacitor 300 is shown mounted onto a hermetic terminal of an active implantable medical device 10, having a plurality of terminal pins 12 extending through passageways 314 of the capacitor 300. The device 10 could comprise a lead wire in which terminal pins 12 are engaged in a corresponding socket or lead wire or the like. In any event, regardless of the device 10 that the capacitor 300 is used in association with, the capacitor 300 serves to attenuate electromagnetic interference signals within a desired range.

With reference to FIGS. 8 and 9, similar to the capacitor 100 illustrated in FIGS. 1 and 2, the capacitor 300 includes a dielectric body 312 comprised of ceramic, glass, or other selected and desired dielectric material. In this instance, there are four passageways 314 extending through the dielectric body 312. Each passageway 314 includes a metallization 308 such that the terminal pins 12 can be conductively coupled thereto, such as through soldering, or other appropriate means. A set of active electrode plates 302 has ends which are conductively coupled to the inner metallization 308. A set of ground electrode plates 304 are conductively coupled to the outer metallization 310. It will be appreciated by those skilled in the art that the terms inner and outer are relative, the important aspect being that the active electrode plates 302 have an end terminating at the passageway 314, and the ground electrode plate set 304 having a portion terminating at a point spaced from and in electrical isolation from the active electrode plate termination 308. Typically, however, the ground electrode plates 304 terminate at the outer metallization 310.

Figure 10:
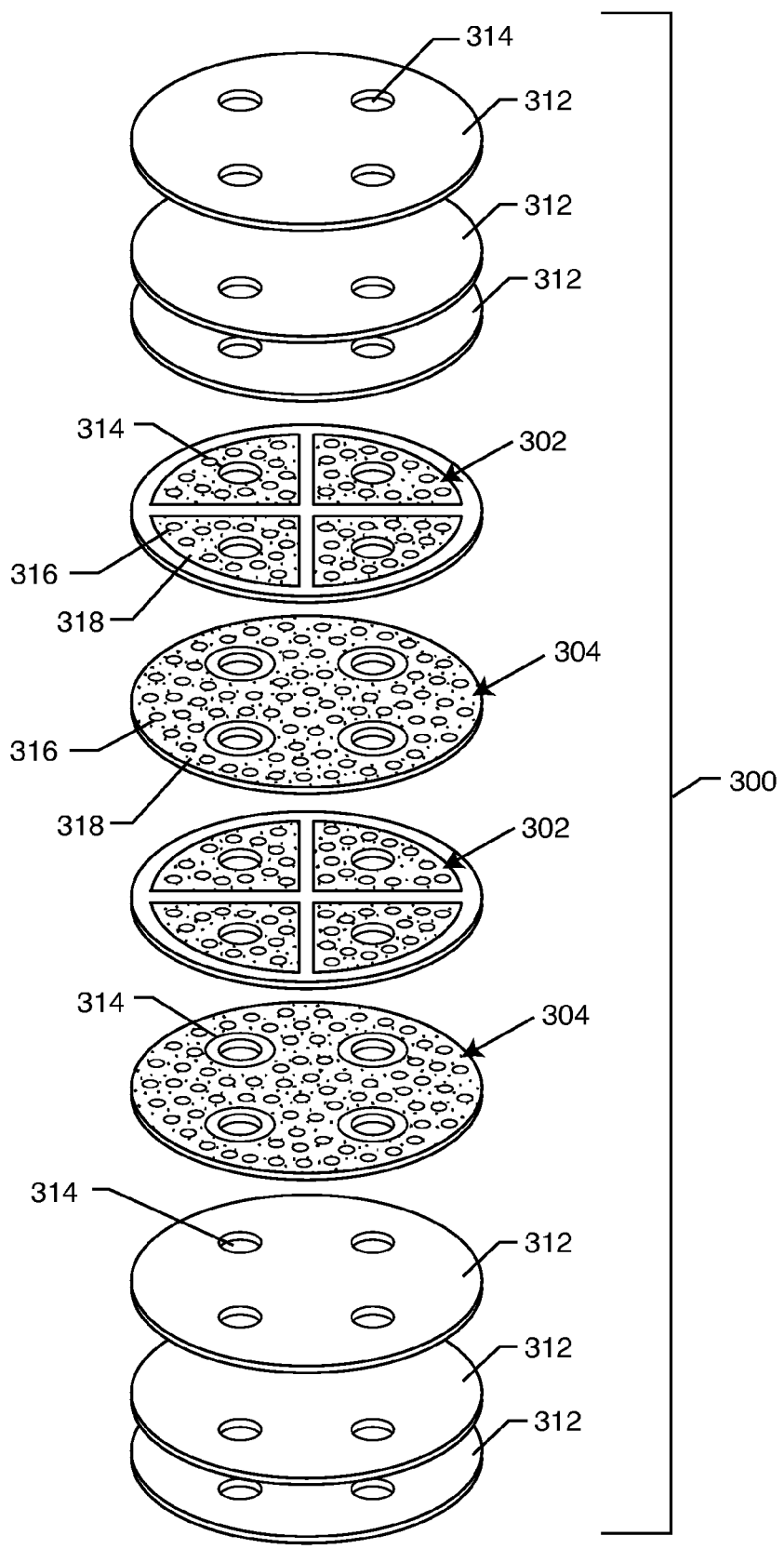
FIG. 10 is an exploded perspective view of the quadpolar feedthrough capacitor of FIGS. 8 and 9.

With reference to FIG. 10, the quadpolar capacitor 300 is constructed in a similar manner as the unipolar capacitor 200 illustrated in FIG. 3. That is, there are a plurality of layers or plates of dielectric material 312 forming the dielectric body 312 of the capacitor 300. In alternating arrangement are active and ground electrode plates 302 and 304. Apertures 314 through each of the layers or plates align in the fully assembled form to create the passageways 314. Once again, the conductive electrode ink material 318 has voids 316 formed therein (which can be of different sizes, configurations and patterns, as discussed above) so as to increase the resistivity or equivalent series resistance of the electrode plate 302 and/or 304, and thus the capacitor 300. Thus, it can be seen that the creation of the voids 216 and 316 can be formed in a variety of different feedthrough capacitor designs and configurations to achieve the intended result of reducing or eliminating the self-resonant dip of the capacitor. It is well known in the prior art that bipolar, quadpolar, hexpolar, or as many passageways as one desires, can be built into the capacitor. The teachings of the present invention are not limited by the capacitor configuration, and thus also applies to prior art mutlipolar feedthrough capacitors.

The methodology for controlling the capacitor equivalent series resistance can relate to the basic formula:

$$R = \frac{\rho \ell}{A}$$

Where R equals the resistance in ohms, ρ (Rho) is the resistivity in ohm centimeters, l is the length in centimeters, and A is the cross-sectional area of the conductor in square centimeters.

From this formula, one can see that by making the Rho (ρ) higher would mean building capacitors with electrode plates that have higher resistivity.

There are a number of electrodes that are well known in the art including base metal electrodes (nickel), palladium silver electrodes or palladium electrodes, platinum electrodes or ternary electrodes consisting of gold, platinum or palladium. Platinum is preferred because platinum inherently has a very high volume resistivity. However, any of the other aforementioned electrode materials could also be used. This is because electrode resistivity is controlled by a blending of powders, a binder material and the loading of metal. By controlling the ratios of these various materials, one can control the overall conductivity of the finished electrode plate. In the present invention, the metal loading would be relatively minimized so as to relatively maximize the electrode's resistivity. This is in direct contrast to the prior art wherein it is desirable to minimize electrode resistivity for other reasons. Therefore, in the present invention a balance is drawn between the metal loading sufficient to eliminate or reduce the self-resonant dip characteristics of the feedthrough capacitor while at the same time providing a low enough resistance for it to properly operate, particularly in the presence of AC power signals.

Another way to further increase the resistivity of electrode plates is to deliberately add capacitor dielectric material to the electrode ink. In general, this is the same dielectric material that is used to form the spacing between the active and ground electrode plates. One can control the amount of dielectric material that is added and thereby have a wide control over the resulting resistance of the electrode plate.

Moreover, one can control the resistance of capacitor termination material, which is either a plating or a silver-fritted or metal-fritted glass, by controlling the metal loading. In other words, resistance can be added at the edge point of the electrodes to its metallization surface by controlling the resistivity of the termination material itself. This can be done either at the outside diameter or the inside diameter or both.

With reference now to FIGS. 11-13, and in a manner similar to that explained in connection with FIGS. 6 and 6A, one can also control the resistivity of the capacitor electrode plates by controlling their cross-sectional area. The cross-sectional area is given by its width (w) and length (l), the product of which equals the cross-sectional area A of the conductor in square centimeters. As illustrated in FIGS. 11-13, the feedthrough capacitor 400 has a plurality of passageways 414 extending through the dielectric body 412. Metallizations 408 line the passageways 414, for convenient connection to terminal pins, etc. Active electrode plates 402 are conductively coupled to the metallization 408. Ground electrode plates 404 are conductively coupled to metallization 410. As illustrated, the electrode plates 402 and 404 have a relatively large width w with respect to length l. Decreasing either the width or the length decreases the cross-sectional area A, and thus increases the resistance R.

Although one can control the resistivity of the capacitor electrode plates 402 and 404 by controlling their cross-sectional area, as a practical matter in many cases one does not really have control over the length or width of the electrode as a certain amount of effective capacitance area is required to achieve the capacitance required for the feedthrough capacitor design. In such cases, one may instead control the thickness of the electrode plates 402 and 404. By controlling silk screen sizes and particle sizes, one can lay down a very thin electrode. This has the effect of changing the electrode resistance. Increasing the electrode resistance ρ (Rho), effectively increases the resistance R of the capacitor, decreases its Q, and serves to reduce or even eliminate the capacitor's self-resonance dip if done in a controlled and precise manner. Thin electrodes are in the 0.5 to 10 micron range.

Yet another method for increasing the equivalent series resistance of the capacitor is to form the dielectric body 212, 312, 412, etc. from a material having high dielectric loss tangents at a selected frequency.

With reference now to FIG. 14, yet another method for increasing the effective resistance of the capacitor is to include a resistor element R in series with the capacitor C. The resistor may be a distributive resistance between the capacitor termination material and the contact point of the electrode.

Figure 15:
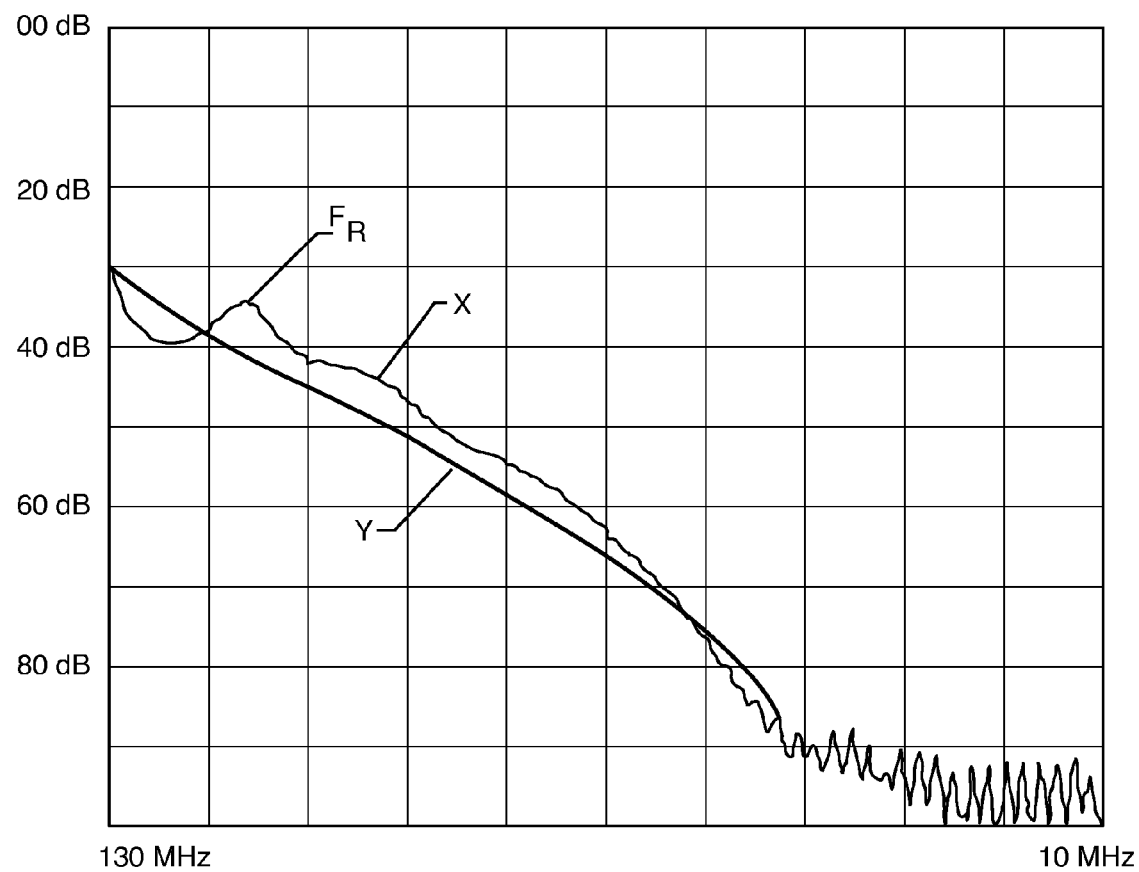
FIG. 15 is a graph comparing a standard feedthrough capacitor's self-resonance insertion loss dip with the performance of a capacitor manufactured in accordance with the present invention.

With reference now to FIG. 15, a graph is provided with two different curves X and Y. Curve X is a typical prior art feedthrough capacitor exhibiting a resonant dip $F_R$, which as previously mentioned is highly undesirable in that it causes the insertion loss to degrade at that point. Curve Y is an ideal curve wherein the ESR, or capacitor Q has been ideally controlled through the herein described methods to eliminate, or at least substantially reduce, the resonant dip and provide a nearly ideal capacitor performance curve versus frequency. As one can see, at the resonant dip frequency, there is a nearly 10 dB improvement in insertion loss at that point. This is very important in broadband EMI filter applications so that the filter performance is not degraded. Thus, by configuring enough series resistance in the electrode plates, or by the other methodology as described above, one can prevent the self-resonant dip from occurring, which will greatly improve the overall filtering effectiveness of the EMI filter.

Although several embodiments have been described in some detail for purposes of illustration, the principles described herein are widely applicable to various feedthrough capacitor technologies and various modifications may be made without departing from the scope and spirit of the invention. For example, for wound feedthrough capacitors using layers of dielectric film and layers of aluminum foil electrodes, it will be obvious to those skilled in the art that the resistivity of the aluminum foil electrodes can be increased by the addition of holes, using higher resistivity alloys, and other concepts of the present invention. Accordingly, the invention is not to be limited, except as by the appended claims.

What is claimed is:

1. A feedthrough capacitor, comprising:
a dielectric body having a passageway therethrough;
an active electrode plate disposed within the body and having an end terminating at the passageway; and
a ground electrode plate disposed within the body in spaced relation to the active electrode plate, the ground electrode plate having a portion terminating at a point spaced from and in electrical isolation from the active electrode plate termination;
wherein capacitor Q is relatively minimized and equivalent series resistance of the capacitor relatively increased to reduce or eliminate self-resonance insertion loss dip of the capacitor.

2. The feedthrough capacitor of claim 1, wherein the active electrode plate includes voids therein.

3. The feedthrough capacitor of claim 2, wherein the active electrode plate includes an outer boundary, and an inner boundary adjacent to the capacitor passageway, wherein the voids are disposed between the outer and inner boundary.

4. The feedthrough capacitor of claim 2, wherein the voids comprise apertures, gaps, slits or spokes formed in the active electrode plate.

5. The feedthrough capacitor of claim 2, wherein the voids comprise a pattern of voids formed in the active electrode plate.

6. The feedthrough capacitor of claim 1, wherein the ground electrode plate includes voids therein.

7. The feedthrough capacitor of claim 6, wherein the ground electrode plate includes an outer boundary, and an inner boundary adjacent to the capacitor passageway, wherein the voids are disposed between the outer and inner boundary.

8. The feedthrough capacitor of claim 6, wherein the voids comprise apertures, gaps, slits or spokes formed in the ground electrode plate.

9. The feedthrough capacitor of claim 6, wherein the voids comprise a pattern of voids formed in the ground electrode plate.

10. The feedthrough capacitor of claim 1, wherein the active electrode plate is of a relatively reduced thickness.

11. The feedthrough capacitor of claim 10, wherein the active electrode plate is between 0.1 nanometer and 10 microns in thickness.

12. The feedthrough capacitor of claim 1, wherein the ground electrode plate is of a relatively reduced thickness.

13. The feedthrough capacitor of claim 12, wherein the ground electrode plate is between 0.1 nanometer and 10 microns in thickness.

14. The feedthrough capacitor of claim 1, wherein the active electrode plate is comprised of a conductive material having a relatively high resistivity.

15. The feedthrough capacitor of claim 14, wherein the active electrode plate is comprised of base metal electrodes (nickel), palladium silver electrodes or palladium electrodes, platinum electrodes or ternary electrodes consisting of gold, platinum or palladium.

16. The feedthrough capacitor of claim 1, wherein the ground electrode plate is comprised of a conductive material having a relatively high resistivity.

17. The feedthrough capacitor of claim 16, wherein the ground electrode plate is comprised of base metal electrodes (nickel), palladium silver electrodes or palladium electrodes, platinum electrodes or ternary electrodes consisting of gold, platinum or palladium.

18. The feedthrough capacitor of claim 1, wherein the active electrode plate has a greater length than width.

19. The feedthrough capacitor of claim 1, wherein the ground electrode plate has a greater length than width.

20. The feedthrough capacitor of claim 1, wherein the active electrode plate is comprised of a conductive material having a dielectric material added thereto.

21. The feedthrough capacitor of claim 20, wherein the conductive material comprises electrode ink having dielectric powder added thereto.

22. The feedthrough capacitor of claim 1, wherein the ground electrode plate is comprised of a conductive material having a dielectric material added thereto.

23. The feedthrough capacitor of claim 22, wherein the conductive material comprises electrode ink having dielectric powder added thereto.

24. The feedthrough capacitor of claim 1, including a resistor disposed in series with the capacitor.

25. The feedthrough capacitor of claim 24, wherein the resistor comprises a distributive resistance between a capacitor termination material and a contact point of the electrode.

26. The feedthrough capacitor of claim 1, wherein the dielectric body comprises a material having high dielectric loss tangents at a selected frequency.

* * * * *